United States Patent [19]
Haswell

[11] Patent Number: 5,454,797
[45] Date of Patent: Oct. 3, 1995

[54] COMBINED PELVIC TRAY, WORKSTATION AND FLUID COLLECTION DEVICE

[76] Inventor: John N. Haswell, 1255 N. Gulfstream Ave., Apt. 508, Sarasota, Fla. 34236

[21] Appl. No.: 289,205

[22] Filed: Aug. 12, 1994

[51] Int. Cl.$^6$ .................................................. A61M 1/00
[52] U.S. Cl. ........................ 604/317; 604/356; D24/183; 206/564
[58] Field of Search ................... 4/144.1–144.4; 604/317, 356, 357; 206/564, 570; D24/183, 184

[56] References Cited

U.S. PATENT DOCUMENTS

| | | | |
|---|---|---|---|
| 1,822,206 | 9/1931 | Ferguson | D24/183 |
| 3,199,507 | 8/1965 | Kamm . | |
| 4,160,505 | 7/1979 | Rauschenberger | 206/564 |
| 4,559,937 | 12/1985 | Vinson | 604/317 |
| 4,616,642 | 10/1986 | Martin et al. | 604/356 |

*Primary Examiner*—Jerome L. Kruter
*Attorney, Agent, or Firm*—Browdy and Neimark

[57] ABSTRACT

A disposable laminar device for collecting body fluids during obstetric, gynecologic, proctologic or urologic procedures or examinations is formed from sheet plastic. The device includes a planar area which is placed on the edge of an examination table, with the patient's buttocks on top. The patient's weight holds the device, but it may also be clipped to the table. Projecting outward from and cantilevering off the table edge is a collection region of the lamina, contiguous with the planar area. The collection region includes a drain portion which receives and directs fluids draining from the perineal area of the patient into a cup integrally formed in the lamina. The drain portion is bordered by a raised ridge or dike which prevents fluids from spreading under the buttocks onto the planar area. The collection region also preferably includes a flat work area and receptacles formed therein to hold solutions, instruments, swabs, and the like. The receptacles may be sealed prior to use, for holding solutions or for sterility.

16 Claims, 2 Drawing Sheets

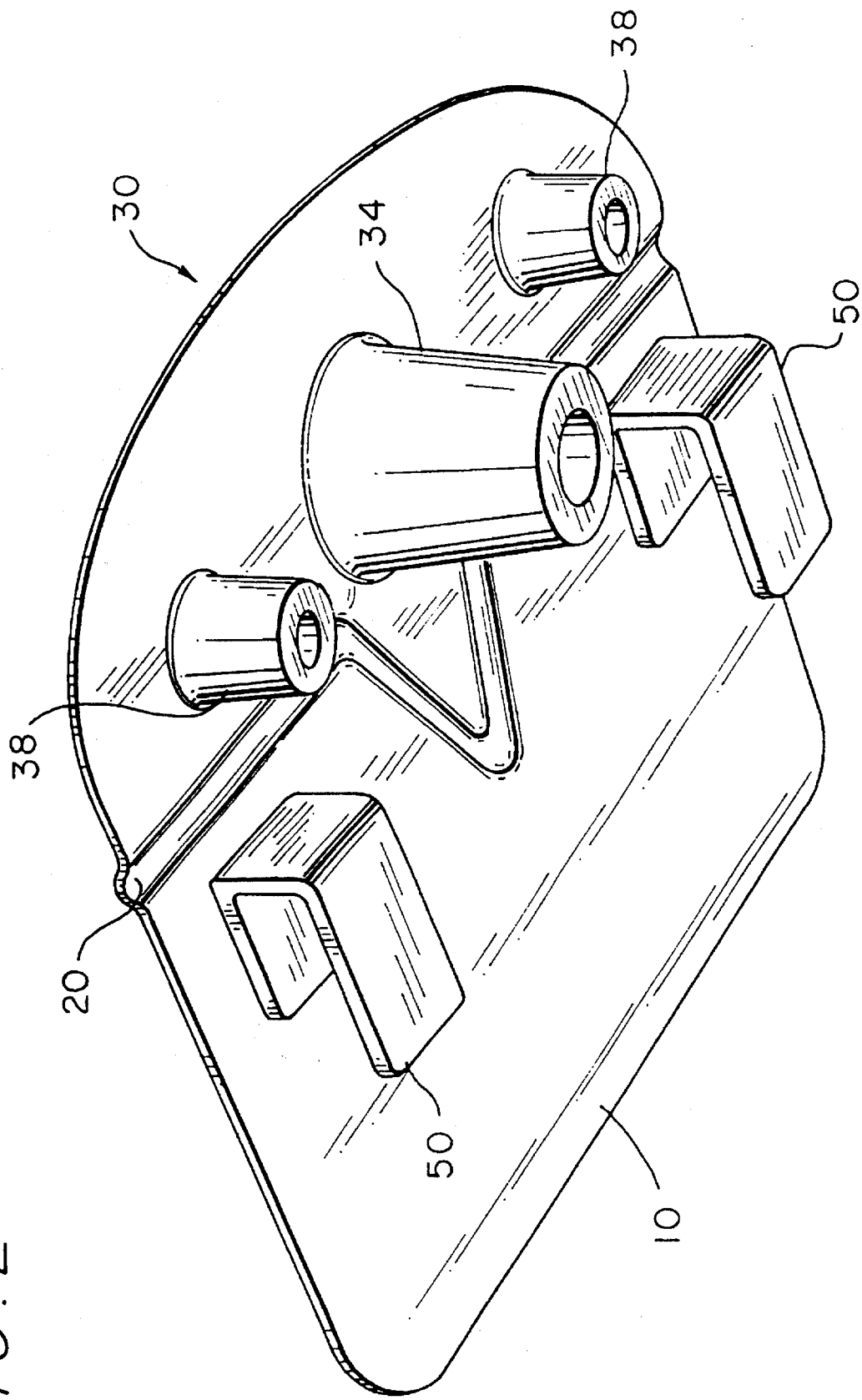

COMBINED PELVIC TRAY, WORKSTATION AND FLUID COLLECTION DEVICE

FIELD OF THE INVENTION

The present invention relates to devices for collecting body fluids during obstetric, gynecologic, proctologic or urologic procedures or examinations. The invention also relates to devices for holding instruments during such procedures or examinations.

BACKGROUND OF THE INVENTION

Medical examinations or other procedures conducted in the perineal area are typically performed with the patient's buttocks resting on the edge of an examination table, the patient's legs in stirrups, and the physician sitting on a chair between the patient's legs. The patient's position is usually such that the perineum is directly over the edge of the table, which allows full support of the weight of the lower body while allowing the physician good access.

Often there is a loss of blood or other body fluids during a procedure. Surgery, non-surgical gynecologic examinations conducted during menses, and other procedures all tend to spread body fluids or mixtures of body fluids and other fluids, such as rinses or topical anesthetics.

The table, on which the patient's buttocks rest, will become covered with body fluids as a result of drainage from the vagina, urethra, or anus. The fluids will drip over the edge and also seep under the buttocks by capillary action and will be smeared about by the patient's buttock movements. Fluids will run off waxed table paper and will soak through porous table paper. The commonly-used plastic-backed paper towels have limited soaking capacity and may not work well when draped vertically over a table edge.

Instruments, swabs, and other items used during the procedure become wetted with body fluids. They are quite likely to drip onto the floor or other surfaces when moved away from the patient's body for disposal or for temporary placement on a work surface.

The resulting mess is undesirable for several reasons.

First, current OSHA regulations called "universal precautions" mandate that health care workers collect, contain, and dispose of all bodily fluids/secretions.

Second, these OSHA regulations further mandate that any spillage of these bodily fluids be cleaned up accordingly in a specific manner after the procedure. This takes time which could be better spent, increases the interval between patients, and may require extra staff. Cleanup is also unpleasant and can be a hazardous task for health care workers. The dangers are slipping and falling, and possible infection with HIV virus or other disease agents present in the body fluid.

Third, the cleanup requires the use of strong chemical cleaners that kill HIV; the use of such cleaners is now mandated by OSHA regulations. The contaminated room is thus closed down and not usable for a period of time required for the chemical cleaners to decontaminate the cleansed surfaces. The cleaners leave an unpleasant odor. The next patient is liable to be offended or made nervous by the strong and unusual smell.

In gynecology the problems associated with menstruating patients lead to frequent re-scheduling of appointments when women begin menstruating at the time scheduled for the visit. The causes are patients' embarrassment, physicians' and nurses' concerns about HIV, and staff reluctance to clean up menstrual blood.

The ideal device to solve these problems would collect body fluids, prevent drips, and keep fluids from contact with the examination table. Such a device would be either disposable or easily cleaned and sterilized, and would protect health workers and reduce patient embarrassment.

Several prior art devices deal with collecting body fluids or with table-top or table-edge medical procedures.

U.S. patent to Kamm, U.S. Pat No. 3,199,507, discloses a blood loss measuring device used during obstetrical operations. This device is mounted on one end of the table top for positioning underneath the patient with a tube extending downward into a glass receptacle. The part of the device between the table top and the patient has no provision for receptacles to hold instruments, solutions, and the like. The portion of the device contacting the patient and channeling fluid flow is not rigid but appears to be made of a flexible fluid impervious web material.

Kamm's device is intended to measure blood loss volume, not to contain fluids; the containment is incidental, and no precautions are taken for reducing the spread of fluids or the number of items wetted. Six or seven different items will be contaminated with blood after its use, and each will need to be separately cleaned. Furthermore, Kamm's fluid impervious web 18 includes a peripheral dike 20 to contain fluids. There is no provision for preventing fluids from seeping under the patient's buttocks.

Mubeim, in U.S. Pat. No. 3,575,225, discloses a sterile specimen container comprising a rigid handle-rim-lid and a flexible transparent bag marked with gradations that attaches to the rim. The handle can be held in surgical operations or inserted between the patient and the surgical table (column 2, lines 20–24). The only receptacle is the flexible bag. There is no disclosure of additional instrument or solution bearing receptacles. Mubeim shows a tapered groove 18 which serves as a body fluid collecting channel (col. 5, line 16). The handle-rim-lid unit of Mubeim is not necessarily disposable. Thermosetting plastics, metal and fiberboard are the materials specified for it. At col. 5, line 3, injection molding for the rim/lid is taught; Mubeim does not teach stamping, and his device is not adaptable to stamping.

Nielsen, in U.S. Pat. No. 4,080,968, discloses a combination obstetrical support and receptacle for placement on a bed or other support surface. This device provides a work area positioned underneath the vagina that can also contain body fluids. A supporting surface, on which the woman's buttocks and lower back are supported during childbirth, is integrally formed with the work area. There are no provisions for additional instrument, equipment, solution or solid waste receptacles. Furthermore, Nielsen's device does not appear to be positioned at the edge of a support surface such as an examination table. It serves merely as a seat or support for the patient. The portion of Nielsen's device under the buttocks is not thin or planar.

Haswell, in U.S. Pat. No. 4,076,017, teaches an end portion 14 intended to be placed underneath the buttocks of the patient. Receptacles 18 and 23 are designed to collect amniotic fluid and blood from the patient during childbirth.

Philippi et al., in U.S. Pat. No. 2,739,858, disclose a self-leveling tray for operating tables. Philippi et al. further reveals in column 2, lines 45–50, that the tray can be used with certain obstetrical or examining tables where items such as instruments are accessible. There is no elaboration as to whether the instruments are meant to be large (such as monitors) or can be used for hand held medical instruments/ implements; the tray may serve to accommodate both types of medical instruments.

Watson, in U.S. Pat. No. 4,266,669, discloses a disposable tray for use by anesthesiologists and for positioning at the end of an operating table. This disposable tray includes a central compartment for receiving the patients head and an arrangement of compartments and recesses for holding medical instruments and medications on both sides of the central compartment.

U.S. Pat. No. 4,160,505, issued to Rauschenberger, discloses a urethral catheterization tray that is provided as a sealed sterile, self-contained catheterization package. There are compartments for holding absorbent pads as well as an area for transferring urine collected in a drainage bag to a specimen container positioned in a recess provided in the tray. Spillage is contained (col. 2, lines 61–63).

Other U.S. patents are: U.S. Pat Nos. Des. 304,759 (McCloskey); Des. 322,855 (Tabuchi); Des. 323,560 (Boyce et al.); 3,646,938 (Haswell); 4,219,035 (Deconinck); 4,457,502 (Beach); 4,501,363 (Isbey, Jr.); 4,880,418 (Tramont); 4,936,836 (Weickgenannt); 4,968,013 (Kuck); 5,062,531 (Coy); 5,078,705 (Edwards et al.); 5,092,859 (Everett et al.); and 5,279,603 (Everett et al.)

SUMMARY OF THE INVENTION

It is an object of the present invention to collect and contain body fluids, such as vaginal fluids.

It is another object of the invention to prevent the spread of body fluids during procedures so as to reduce the need for clean-up.

It is a further object of the invention to facilitate disposal of body fluids and supplies.

It is yet a further object of the invention to satisfy OSHA requirements relating to body fluids.

It is still another object of the invention to provide a workstation and platform for gynecologic or similar procedures.

It is yet another object of the invention to provide a holding place for medications, instruments, and supplies used in gynecologic or similar procedures.

The above and other objects of the present invention are achieved by the substantially rigid device of the present invention. The device is tray-like, formed from substantially rigid sheet material such as plastic. Raised and depressed ridges and cups collect and contain body fluids, or fluids contaminated with body fluids, during gynecologic or similar procedures.

A planar area of the device is disposed under a patient's buttocks as she sits on the edge of an examination table, so that the planar area is held between the buttocks and the table. Contiguous to the planar area is a collection region where the fluids are contained. The collection region overhangs and cantilevers off of the edge of the table. A drain portion of the collection region is disposed under the perineum to collect fluids. The drain portion preferably slopes downward to a cup, which cup is a depressed portion of the collection region.

A raised ridge or dike runs along the border of the planar area, separating it from the collection area. The dike includes a perineal indentation which borders the drain portion. The dike prevents fluids from spreading into the planar area by acting as a gravity dam, and also by acting as a seal where the patient's buttocks press against it.

The collection region includes a flat table-like area which can serve as a workstation. It also includes one or more other receptacles preferably made as integral depressions in the device, for holding implements, supplies, and solutions. In a preferred embodiment the collection area includes one substantially centrally disposed collection cup and two other receptacles for holding implements, supplies and/or solutions. Other, specialized, holding gear may be included for particular instruments or procedures.

Clips or other holding means may be attached to the device for stabilizing it on the examination table.

The present invention not only collects fluids which may drain from the perineal area of the patient, but also holds instruments or implements as well as liquid or solid supplies and materials which may be used in the course of the examination at the immediate area of the procedure. It thus prevents drips and minimizes cleanup. The device is preferably disposable, so that the device, fluids, and trash on the workstation can all be disposed of at once, with minimal handling and risk of infection.

BRIEF DESCRIPTION OF THE DRAWING

FIG. 2 is a perspective view of the invention from below, showing clips attached to the lower surface.

DETAILED DESCRIPTION OF THE PREFERRED EMBODIMENTS

Figure 1:
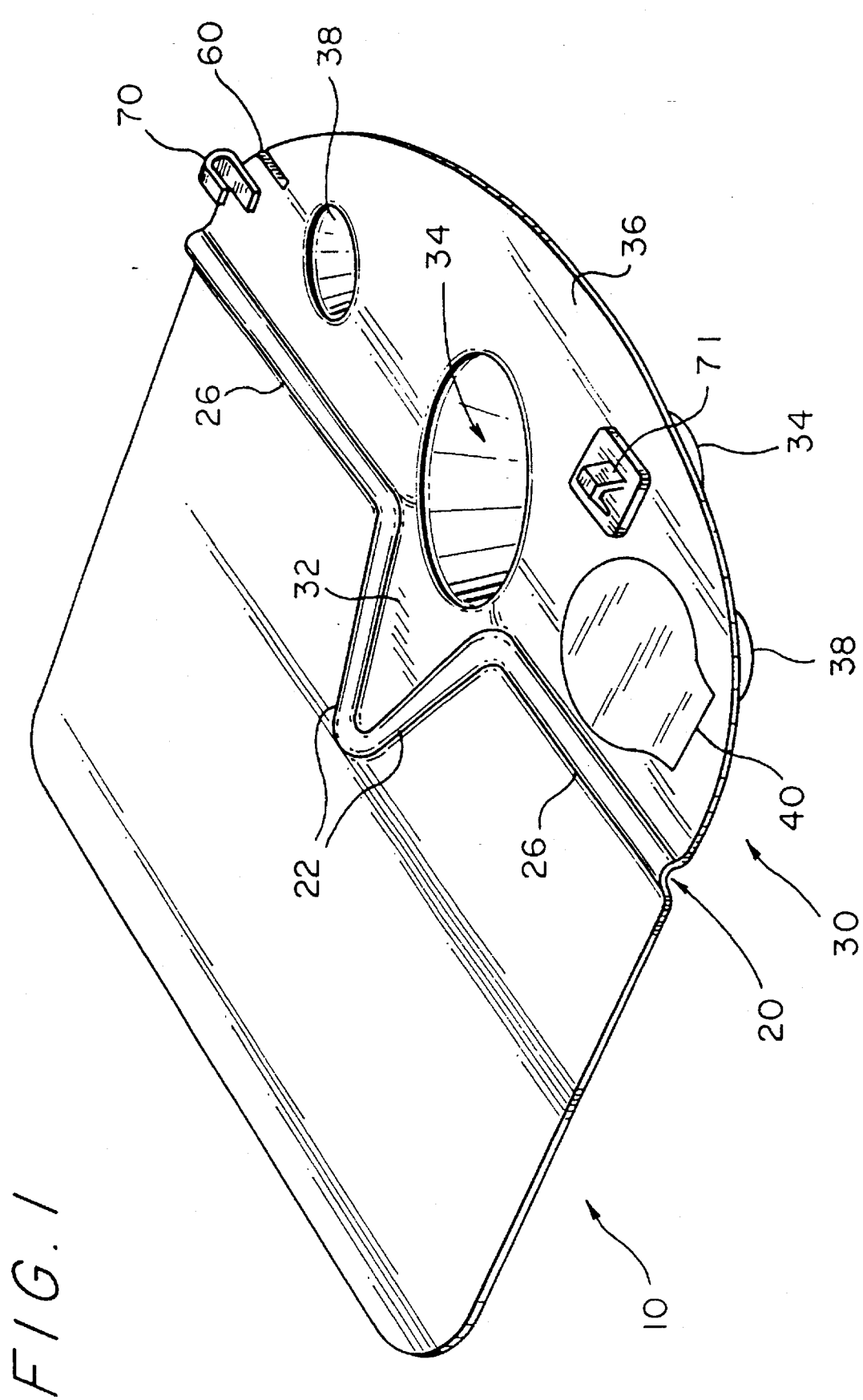
FIG. 1 is a perspective view of the invention from above, showing an upper surface of the invention.

The present invention, a combined pelvic tray, workstation and collection device for body fluids, is shown in FIG. 1. It is intended for obstetric, gynecologic, proctologic, or urologic examinations and procedures in which fluids drip from the perineal region of the body, e.g. from the vagina, anus, urethra, etc. The device of the present invention collects and contains the fluids to avoid danger and mess; as such, in use it has an orientation to gravity. The upper side is depicted in FIG. 1 and the lower side is depicted in FIG. 2.

The device includes a generally planar area 10 which in one mode of use is disposed under the patient's pelvis, i.e., between a patient's buttocks and the table beneath. The remaining region 30 of the device is that region which is intended to overhang and cantilever off of the table when in use. Region 30 serves as a fluid collection area for collecting and containing fluids draining from the periheal area of the patient when in use, such as during a gynecological examination, as well as a workstation for the doctor and a tray for holding instruments, implements or supplies, either solid or liquid. This combined collection area, workstation and tray area 30 will be referred to hereinafter as collection region 30. The collection region 30 is contiguous to the planar area 10. A raised ridge or dike 20 separates the planar area 10 and the collection region 30 and at least partially bounds the collection region.

In a preferred embodiment, the device is approximately one foot wide. The collection region 30 is about four inches long and the generally planar area 10 is about eight inches long.

The planar area 10, dike 20, and collection region 30 preferably are all composed of a single sheet of laminar material such as 40-mil styrene plastic sheet or light-gauge stainless steel. The material is chosen so as to be substantially rigid after forming such that the collection region 30 can be self-supporting when cantilevered off the edge of an examination table. The device is formed by molding, thermoforming, vacuum forming, stamping, forging, coining or like processes into the shape depicted in FIG. 1.

The collection region 30 includes a cup 34 formed as a depression, which may be about three inches deep from the planar surface 36. The cup 34 contains fluids by gravity when the planar area 10 is horizontal. Immediately adjacent the cup 34 is a shallow, dished drain portion 32 of the collection region 30 whose bottom surface preferably slopes toward the cup 34 so that fluids will run from the drain portion 32 into the cup 34. The drain portion 32 is bordered by the cup 34 in front and by the dike 20 in back. The cup 34 may be graduated for volume and may be conical or tapered for stacking of the devices.

Here, and in the following claims, the word "cup" means a container or receptacle with only one opening, that is, with a closed bottom.

The dike 20 is preferably formed as a ridge or rib by the same stamping or molding operation which forms the cup 34 and other parts of the device, and whose outline has in cross-section an inverted V-shape or inverted U-shape. The dike 20 may alternatively be formed by other conventional means, such as fastening a separate elongated piece onto the surface of the planar area 10. As the name implies, the dike's function is to contain fluids in the collection region. The dike 20 preferably is comprised of two collinear straight segments 26 and two angled segments 22 which are aligned into a V shape (as seen in plan view). The indentation in the line of the dike 20 composed of the two segments 22 is directly below the perineal region of the patient when the device is in use. This perineal indentation of the dike 20 borders the drain portion 32. All the segments of the dike 20 are joined at their ends, so that the dike 20 forms a continuous border between the area 10 and the region 30. In the preferred embodiment depicted in FIG. 1, the two collinear straight segments 26 lie generally above and parallel to the table edge when the device is in use. The indentation is preferably approximately three inches deep and about as wide at the open end thereof as the diameter of the collection cup 34.

The dike 20 operates in two ways. First, it resists the spread of fluids by flowing over the surface of the collection region 30 by acting as a dam; second, it seals against the patient's buttocks. Segments 22 are directly under the buttocks, which bear downward with considerable weight against them. The high localized force along the ridge line of the segments 22 cause the buttocks to act as a gasket to resist fluid seepage into the area 10. Such seepage creates a mess, makes the patient uncomfortable, and can cause embarrassment. Segments 22 are preferably approximately ¼ inch high.

In contrast, the prior-art peripheral raised portion 20 of Kamm does not operate efficiently to prevent soiling of the table. With the Kamm device the patient's buttocks become wet to the very edge of the web 18, so that any lateral movement will spread fluid onto the table. Moreover, the raised portion 20 is placed so that the pressure of the buttocks is both less and more variable than it is along the segments 22 of the present invention.

The perineal indentation formed by the segments 22 may be alternatively formed in a different outline, and may include height variations. The dike 20 be interrupted by a short gap at the point where the coccyx bears against the device (at the apex of the perineal indentation) for greater comfort without leakage. The dike 20 and the perineal indentation of the dike 20 are not limited to any particular shape. The dike 20 may be in plan view a single smooth curve or two mirror-image smooth curves, rather than distinct perineal sections or straight segments divisible into segments 22 and 26. The dike 20 may be continued around the perimeter of the collection region 30 or be made continuous with an upturned edge of the collection region 30. It may alternatively or additionally be made to surround the cup 34 in order to prevent flow of fluids from the area of drain portion 32 and collection cup 34 to other areas of collection region 30 which serve as a workstation.

The device thus functions to collect fluids from the vagina or other orifice into the drain portion 32 and the cup 34, and to contain them in those parts of the device. Seepage under the buttocks is prevented by the perineal indentation of the dike 20.

A dripping syringe, speculum, swab, applicator, or other instrument soaked with body fluids can spread such fluids onto the floor or the physician's clothing, even when the fluid coming directly out of the body is Contained. Accordingly, the present invention includes a work surface 36 on the collection region 30 and receptacles 38 for holding the various implements used in the procedure. These implements need never move from above the collection region 30, and so do not drip except there. Any number of receptacles 38, of any shape, may be adapted to holding special equipment for various procedures, For example, the work surface 36 and the receptacles 38 may be used to hold instruments for biopsy or hysterosalpingogram, used gloves, speculum, applicators, syringes, silver nitrate sticks, large swabs, and the like. Preferably, two such receptacles 38 are present, as shown in the figures.

At the end of the procedure, the patient lifts her or his buttocks from the planar area and the device of the present invention is removed. Waste such as gloves and wipes may be left on the device and the whole disposed of in a safe, OSHA-regulated container. Alternatively, the fluids and refuse may be disposed of and the device rinsed and sterilized for the next use.

The receptacles 38 may be filled with any of various solutions which may be used during examinations, such as gynecological examinations, or medical procedures. Examples of such solutions are Monsel's solution, vinegar, Lugol's solution, Condylox solution, Podophyllin solution, Trichloroacetic acid, and Betadine or other cleansing solutions. One or more of the receptacles 38 of the present invention may be pre-filled with any such liquid solution or reagent at the time of manufacture, or thereafter, with such filled receptacles being sealed by a peel-off sealant cover 40, shown in FIG. 1. The sealant cover 40 acts as a lid to contain such solutions within, ready for use. The receptacles 38 and collection cup 34 may be graduated.

The device may also include a slit 60 to hold electric cords or tubing and clips 70 and 71 to hold surgical instruments or electro-surgical electrodes. Other devices or shapes, adapted to various instruments or supplies, may also be used. Together with the work surface 36 and receptacles 38, a complete workstation for any procedure can be constructed in the collection region 30.

The device may be disposed under the patient's buttocks to hold it in place, as described above. The device may also be placed at the edge of an examination table with the collection region 30 resting partially on a pull-out extension and the cup 34 and receptacles 38 in the gap between the table and the extension. The device may also be placed on top of the basin that is contained in the pull-out extension of an examination table.

An optional addition to the device is shown in FIG. 2, which is a view from below rather than from above. The embodiment of FIG. 2 includes one or more clips 50 into which is inserted the edge of the examination table or the table mattress. The clips 50 help prevent the device from moving when the patient elevates her hips. The clips 50 may be formed as shown, or be separate pieces attached by conventional means. Other means of stabilizing the device on the table, such as removable adhesive, are within the scope of the present invention.

The device of the present invention is preferably laminar in that it is formed from a single sheet of material. As such, it can be manufactured from common sheet material by conventional processes or combinations of processes and is very inexpensive to manufacture. Examples of such processes are vacuum-forming, blow-molding, forging, and coining. Moreover, the device stacks (if made with conical cup 34 and receptacles 38 and without clips 70) and is light in weight, so shipping and storage are also inexpensive. The material need not be thick, because the dike 20, cup 34, and receptacle 38 stiffen it; additional stiffening ribs or dike 20 extensions may be added as needed (for example, along the perimeter of the collection area and across the table edge).

Because the device is inexpensive, it can be disposable, which is a safety aid for health workers. The device of the present invention safely contains body fluids which might carry HIV virus; it aids in complying with OSHA requirements; it prevent drips and contamination of examination tables and reduces handling of possibly contaminated fluid; it keeps not only body fluids, but also medical waste and trash such as used swabs, together with the device to allow disposal of all in one motion; and it reduces trash volume and costs by reducing the number and size of absorbent towels that might be needed during a procedure.

The foregoing description of the specific embodiments will so fully reveal the general nature of the present invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A one-piece, unitary, substantially rigid fluid collection and containment device for obstetric, gynecologic, proctologic, or urologic examinations and procedures of a patient on a table, the device having an upper side and a lower side and comprising:

a single generally planar area for disposition between the patient and the table;

a collection region contiguous to the planar area and designed to maintain a substantially coplanar relationship with said planar area when the collection region is cantilevered off the edge of the table and held thereon by weight of the patient, said collection region including a depressed collection cup designed to hold fluids therein and to serve as a fluid collection receptacle for body fluids when the patient's buttocks rest on the planar and the collection region is substantially disposed beneath the perineal area of the patient; and a raised dike intermediate the planar area and the collection region, the dike at least partially bounding the collection region.

2. A device in accordance with claim 1, wherein said collection region further includes, in addition to said depressed cup, a depressed receptacle whereby said depressed receptacle serves to hold liquid or solid supplies or instruments when in use.

3. The device according to claim 2, wherein said receptacle includes a peel-off cover.

4. The device according to claim 2, wherein said receptacle is tapered, thereby allowing stacking.

5. The device according to claim 1, wherein the device is formed of a single continuous non-planar lamina.

6. The device according to claim 5, wherein the device is formed from plastic sheet material.

7. The device according to claim 1, wherein said dike includes a perineal indentation into said planar area, the perineal indentation having, in planar view, a generally V-shape to prevent fluids from seeping onto the planar area when the perineum of the patient is disposed above the perineal indentation.

8. The device according to claim 7, wherein said collection region includes a depressed collection cup proximal the perineal indentation of said dike.

9. The device according to claim 8, wherein said collection region further includes a depressed drain portion intermediate said cup and the perineal indentation of said dike.

10. The device according to claim 9, wherein said drain portion further includes a bottom surface sloping downwards toward the cup when said planar area is horizontal, such that fluids run from said drain portion into said collection cup when in use.

11. The device according to claim 10, wherein said cup is tapered, thereby allowing stacking.

12. The device according to claim 1, wherein said collection region includes a substantially flat work surface.

13. The device according to claim 12, further including a slit in an edge of said flat work surface.

14. The device according to claim 1, further comprising an electric cord clip.

15. The device according to claim 1, further comprising clip means for attaching the device to a table.

16. The device according to claim 15, wherein said clip is attached to an underside of said planar area.

* * * * *